United States Patent
Mandal et al.

(10) Patent No.: US 9,550,708 B2
(45) Date of Patent: Jan. 24, 2017

(54) PROCESS FOR CATALYTIC CONVERSION OF LOW VALUE HYDROCARBON STREAMS TO LIGHT OLEFINS

(71) Applicant: Reliance Industries Limited, Mumbai, Maharashtra (IN)

(72) Inventors: Sukumar Mandal, Haryana (IN); Manoj Yadav, Haryana (IN); Amitkumar Parekh, Gujarat (IN); Asit Kumar Das, Gujarat (IN); Shubhangi Jaguste, Maharashtra (IN); Praveen Kumar Chinthala, Andhra Pradesh (IN); Gopal Ravichandran, Tamil Nadu (IN); Mahesh Marve, Maharashtra (IN); Ajit Sapre, Tampa, FL (US)

(73) Assignee: Reliance Industries Limited, Mumbai (IN)

( * ) Notice: Subject to any disclaimer, the term of this patent is extended or adjusted under 35 U.S.C. 154(b) by 156 days.

(21) Appl. No.: 14/459,690

(22) Filed: Aug. 14, 2014

(65) Prior Publication Data

US 2014/0357912 A1 Dec. 4, 2014

Related U.S. Application Data

(63) Continuation of application No. PCT/IN2012/000289, filed on Apr. 20, 2012.

(30) Foreign Application Priority Data

Feb. 14, 2012 (IN) .......................... 406/MUM/2012

(51) Int. Cl.
*C07C 4/06* (2006.01)
*C10G 11/18* (2006.01)
(Continued)

(52) U.S. Cl.
CPC ................. *C07C 4/06* (2013.01); *C10G 11/18* (2013.01); *C10G 11/182* (2013.01);
(Continued)

(58) Field of Classification Search
CPC .......... C07C 4/02; C07C 4/06; C07C 2529/40; C07C 2529/06; C10G 11/18; C10G 11/00; C10G 11/05
(Continued)

(56) References Cited

U.S. PATENT DOCUMENTS 4,289,606 A * 9/1981 Gladrow ................ C10G 11/05
208/120.1
4,627,911 A * 12/1986 Chen ...................... C10G 11/05
208/120.01

(Continued)

FOREIGN PATENT DOCUMENTS

IN  1955/MUM/2011  7/2011
WO  2011/121613 A2  10/2011
(Continued)

OTHER PUBLICATIONS

International Search Report of PCT/IN2012/000289, mailed Oct. 29, 2012.
(Continued)

*Primary Examiner* — Sharon Pregler
(74) *Attorney, Agent, or Firm* — Collard & Roe, P.C.

(57) ABSTRACT

A process for catalytic conversion of low value hydrocarbon streams to light olefins in comparatively higher yields is disclosed. Propylene is obtained in amounts higher than 20 wt. % and ethylene higher than 6 wt. %. The process is carried out in a preheated cracking reactor having a single riser and circulating an FCC catalyst. The riser is divided into three temperature zones in which different hydrocarbon feeds are introduced. An oxygenate feed is introduced in the
(Continued)

operative top zone in the riser. Heat for the endothermic cracking is obtained by the exothermic reaction of converting the oxygenate feed into gas and/or from a regenerator in which the spent FCC catalyst is burnt.

15 Claims, 1 Drawing Sheet

(51) Int. Cl.
  B01J 29/08    (2006.01)
  B01J 29/40    (2006.01)
  B01J 29/80    (2006.01)
  B01J 29/90    (2006.01)
  B01J 38/30    (2006.01)
(52) U.S. Cl.
  CPC .......... *C10G 11/185* (2013.01); *B01J 29/084* (2013.01); *B01J 29/40* (2013.01); *B01J 29/80* (2013.01); *B01J 29/90* (2013.01); *B01J 38/30* (2013.01); *C07C 2529/06* (2013.01); *C07C 2529/40* (2013.01)
(58) Field of Classification Search
  USPC .. 585/638, 639, 640, 302, 648, 653; 208/46, 208/106, 113
  See application file for complete search history.

(56) References Cited

U.S. PATENT DOCUMENTS

| | | | |
|---|---|---|---|
| 4,927,522 A * | 5/1990 | Herbst | ............... C10G 11/18 208/114 |
| 4,980,053 A | 12/1990 | Li et al. | |
| 5,171,921 A | 12/1992 | Gaffney et al. | |
| 5,846,402 A | 12/1998 | Mandal et al. | |
| 5,981,819 A | 11/1999 | Moeller et al. | |
| 6,797,851 B2 * | 9/2004 | Martens | ............... C07C 1/20 585/639 |
| 7,491,315 B2 | 2/2009 | Eng et al. | |
| 7,601,663 B2 | 10/2009 | Choi et al. | |
| 7,867,378 B2 | 1/2011 | Pinho et al. | |
| 2009/0187059 A1 | 7/2009 | Chewter et al. | |
| 2010/0168488 A1 | 7/2010 | Mehlberg et al. | |
| 2011/0240523 A1 | 10/2011 | Mandal et al. | |

FOREIGN PATENT DOCUMENTS

| | | |
|---|---|---|
| WO | 2013/011517 A1 | 1/2013 |
| WO | 2013/121433 A8 | 10/2013 |

OTHER PUBLICATIONS

Written Opinion of the International Searching Authority of PCT/IN2012/000289, Aug. 14, 2014.

Bernard Lücke et al., CMHC: coupled methanol hydrocarbon cracking Formation of lower olefins from methanol and hydrocarbons over modified zeolites, Microporous and Mesoporous Materials 29, 1999, pp. 146-157.

* cited by examiner

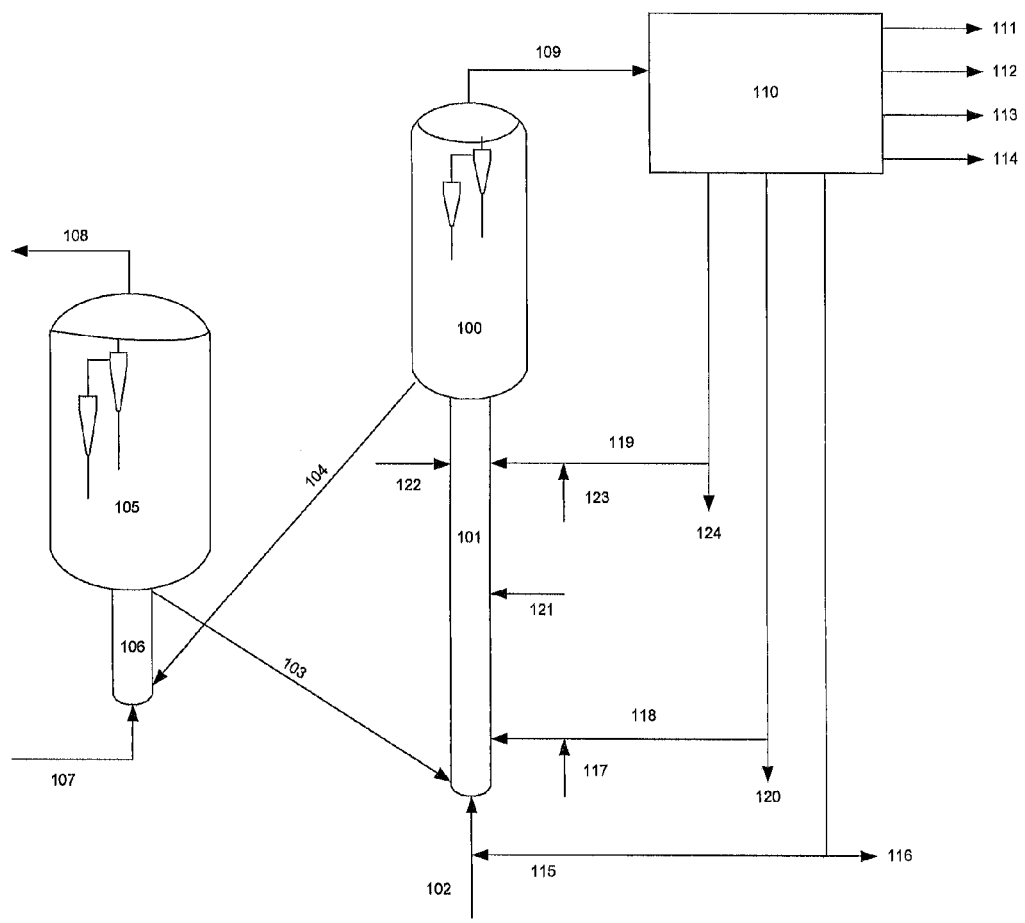

PROCESS FOR CATALYTIC CONVERSION OF LOW VALUE HYDROCARBON STREAMS TO LIGHT OLEFINS

CROSS REFERENCE TO RELATED APPLICATIONS

This application is the Continuation of PCT/IN2012/000289 filed on Apr. 20, 2012, which claims priority under 35 U.S.C. §119 of Indian Application No. 406/MUM/2012 filed on Feb. 14, 2012, the disclosures of which are incorporated by reference.

FIELD OF THE DISCLOSURE

The present disclosure relates to a catalytic cracking process of hydrocarbon feedstock to produce light olefins in high yield, to obtain light olefins in improved yield.

BACKGROUND

Extensive efforts are being made to maximize the production of light olefin such as ethylene and propylene in order to meet the growing demand of light olefins. As used in this specification the term light olefin is deemed to mean ethylene, propylene but not butylene. Generally, propylene and ethylene are produced as by-products (4-6 wt. % propylene and 2-3 wt. % ethylene) while manufacturing fuels such as gasoline, diesel and the like by employing the Fluid catalytic cracking (FCC) process. Propylene is separated from FCC reactor product vapors for getting petrochemical feedstock. However, the separation of ethylene from other FCC products is not very economically attractive due to the lower quantity of the same; therefore, it is used as a refinery fuel gas. Since late nineties, some FCC units have been operating at higher severity to get propylene of 10-12 wt % of the fresh feed. To further increase the propylene yield, different processes have been developed around FCC configuration. Some of them are still operational.

Existing Knowledge

U.S. Pat. No. 4,980,053 discloses a process called Deep Catalytic Cracking (DCC) wherein a preheated hydrocarbon feedstock is cracked over heated catalyst in a reactor to produce light olefins. The obtained gaseous products are separated into ethylene, propylene, butylenes and other components.

As, this process requires 5-10 seconds of contact time, it produces relatively substantial quantity of undesirable products like dry gas.

U.S. Pat. No. 5,846,402 discloses a catalytic conversion of heavy hydrocarbon feedstock to produce high yield of liquefied petroleum gas and light olefins having 3 to 4 carbons. The cracking of feedstock is carried out in a high velocity riser reactor under catalytic cracking conditions that include high catalyst to oil ratio and high riser temperature. The cracking catalyst as disclosed in aforementioned US patent is a solid acid catalyst comprising ultra stable-Y (USY) zeolite, shape selective pentasil zeolite and active matrix. The U.S. Pat. No. 5,846,402 teaches the art of cracking heavy hydrocarbon in a single riser configuration at very high severity.

Further, U.S. Pat. No. 7,491,315 discloses a process of cracking the hydrocarbon in a dual riser configuration. The heavy hydrocarbon like vacuum gas oil cracks in a first riser at relative lower severity to produce products; the products obtained from the first riser i.e. light crack naphtha and $C_4$ stream are then allowed to crack in a second riser at very high reaction severity. The cracking catalyst is a combination catalyst having a conventional FCC catalyst in combination with ZSM-5 catalyst. The process as disclosed in U.S. Pat. No. 7,491,315 is a heat balanced process in which the heat generated by burning the coke deposited on catalyst is utilized further. However, the additional coke precursors are introduced in the riser to obtain heat-balanced condition. The major drawback of two-riser configuration is that it requires an additional catalyst circulation loop including new riser reactor which adds to increased capital expenditure and space.

Mehlberg et. al. in their United States Patent Application 2010/0168488 disclose a process of cracking multiple feedstock in a dual riser reactor vessel. The reason for opting two reactor vessels is argued to be an artifact of equilibrium composition governing the $C_3$-$C_5$ range olefins. While two separate reactors, two separate main columns and gas connection are good to achieve close to equilibrium yield of light olefin and avoid recycling of lower crack-able $C_4$-$C_6$ hydrocarbons, such scheme add to duplication of many equipment/vessel thereby leading to high capital expenditure. There are some "On-purpose" propylene production processes which convert low value naphtha feedstock to light olefins by employing ZSM-5 zeolite based catalyst at very high reaction severity. The light feed stocks make very less catalytic coke on ZSM-5 zeolite based catalyst; therefore, these processes require external heat supply to satisfy heat demand for the endothermic cracking in the riser. In general, fuel oil in combination with heavy oil product, produced in the process, is injected in the regenerator as a source of heat. But, the continuous burning of fuel in regenerator accelerates hydrothermal deactivation of catalyst. Further, some part of feed material is being continuously burned for supplying additional heat which leads to some bearing on process economics. U.S. Pat. No. 7,601,663 discloses a cracking of straight run naphtha to light olefins in a riser at very high riser temperature using ZSM-5 zeolite based catalyst. The heat balance is satisfied by preheating the feedstock in a separate furnace and by burning the fuel oil in a regenerator which further leads to higher hydrothermal catalyst deactivation resulting requirement of higher catalyst make up rate.

U.S. Pat. No. 5,171,921 discloses a new process for converting $C_3$ to $C_{20}$ hydrocarbons to light olefins using ZSM-5 zeolite catalyst having phosphorous. In this process, the production of catalyst coke is very less, therefore, the heat required for endothermal cracking is supplied partially by preheating the feedstock and continuous burning the fuel oil in a regenerator.

Further, U.S. Pat. No. 7,867,378 discloses sequential cracking of ethanol and hydrocarbon wherein ethanol converts to ethylene in a first reaction zone and hydrocarbons to light olefins in a reaction zone in a single riser. Usually, the riser bottom temperature and pressure are very high, ethanol over cracks to lighter gas. In case severity at riser bottom is less, conversion of hydrocarbon to lighters will also be less.

Further, U.S. Pat. No. 5,981,819 discloses a process (Propylur process) that employs adiabatic fixed bed type, similar to that employed in a claus unit, to convert olefin streams of $C_4$ hydrocarbon to light olefin using ZSM-5 type of catalyst.

Other than aforementioned described prior-art processes, methanol conversion processes are also employed to produce light olefins e.g. propylene and ethylene. These conversion processes are characterized by a high exothermicity, depending especially on the methanol conversion rate. These processes employ mostly fixed bed reactor configuration and reactor design is determined by heat control and removal of heat from the process. As it is fix bed process, it needs regeneration in regular frequency.

U.S. Pat. No. 4,627,911 discloses a heat neutral cracking process where exothermic methanol cracking and endothermic gas oil cracking are combined to achieve heat neutrality. The process as disclosed in aforementioned patent is executed without regenerating the catalyst. However, this process requires methanol to be injected preferably upfront of the gas oil to increase the catalyst temperature before gas oil cracking. Also the residence time required in the riser is much higher >6-15 sec with corresponding low WHSV of ~25 hr$^{-1}$. However, to maximize light olefin, it is necessary to minimize riser residence time to minimize H-transfer reactions. Further, the higher temperature (>550° C.) overcracks the methanol leading to unwanted dry gas formation.

Bernhard Lucke et al. (Microporous and Mesoporous Materials 29 (1999) 145-157) disclose a method for simultaneous conversion of $C_4$/N-hexane/naphtha and methanol over ZSM-5 zeolite based catalyst in a fix bed configuration. The combination of endothermic cracking of hydrocarbons and exothermic cracking of methanol having suitable weight ratio produces light olefins under thermally sustained conditions. However, the co-feeding of hydrocarbons and methanol results in 100% conversion of methanol, but less conversion of hydrocarbon. Bernhard further discloses that higher reaction severity increases hydrocarbon conversion, but over cracks olefin to methane. Perhaps, higher temperature and higher residence time over cracks methanol to lighter like methane. However, the co-feeding of hydrocarbons and methanol does not give optimum conversion of both methanol and hydrocarbon and optimum selectivity towards olefins.

Therefore, a process of catalytic conversion of hydrocarbon feedstock having wide range of hydrocarbon feeds in the single riser to produce high yield of lower olefins is provided in the present disclosure wherein the drawbacks of related prior-art processes such as use of a dual reactor system, ill production of desired light olefins and deactivation of catalyst are obviated successfully.

OBJECTS

Some of the objects of the present disclosure, which at least one embodiment herein satisfies, are as follows:

It is an object of the present disclosure to ameliorate one or more problems of the prior-art or to at least provide a useful alternative.

Another object of the present disclosure is to provide a process for catalytic cracking of hydrocarbon feedstock to produce light olefins with compatible higher yield.

Still another object of the present disclosure is to provide a process for catalytic cracking of hydrocarbon feedstock wherein the feedstock is a multi feedstock comprising hydrocarbons of diverse cracking behavior.

Yet another object of the present disclosure is to provide a process for catalytic cracking of hydrocarbon feedstock wherein the cracking is carried out in a single riser under thermo-neutral condition.

Further object of the present disclosure is to provide a thermo-neutral cracking process for obtaining light olefins with compatible higher yields.

Other objects and advantages of the present disclosure will be more apparent from the following description when read in conjunction with the accompanying figures, which are not intended to limit the scope of the present disclosure.

SUMMARY

The present disclosure discloses a thermo neutral catalytic conversion process and catalyst for catalytic conversion of low value hydrocarbon feedstock to improve the yield of light olefins, particularly propylene and ethylene by allowing sequential multizone cracking reaction in a single riser which is divided in high, intermediate and low severity zones for sequential cracking of a wide range of feedstock from $C_4$ to residue. Near thermo neutrality of this process is realized in the overall reaction section by any or both of the following options. (i) Sequential processing of endothermic cracking reaction of $C_4$ to residue, combining with exothermic methanol cracking (ii) Combining low coke making feedstock e.g. $C_4$ to naphtha with high coke making feed stock like residue, slurry oil and the like and then burn off the coke thus produced in separate regenerator to satisfy the heat balance requirement. The process utilities highly stable ZSM 5 as disclosed in PCT application PCT/IN2011/000599 or alkaline metal modified ZSM 5 as disclosed in Indian application no 1955/MUM/2011 in combination with USY, ReUSY or Beta based FCC catalyst. The operational control of each zone is provided and maintained by altering the feed preheat temperature, feed stock flow rate and steam dilution to the combined hydrocarbon stream entering each zone; whereas the desired WHSV in each zone is additionally achieved in the design by altering the riser diameter, length and injection of the hydrocarbon and dilution steam.

According to the present disclosure there is provided a process for obtaining light olefins with comparatively higher yields comprising the following steps:

i. providing a pre-heated cracking reactor having a riser maintained at a pressure in the range of 0.5 to 3 bar, charged with a solid acidic FCC catalyst, said riser being provided with at least three temperature zones; a first zone operative at the bottom of the riser having a temperature varying from 650° C. to 750° C., a second intermediate zone having a temperature varying from 580° C. to 650° C. operative above the first zone and a third zone operative at the top of the riser having a temperature in the range of from 500° C. to 620° C.;

ii. feeding, at a weight hourly space velocity of 0.2 h$^{-1}$ to 50 h$^{-1}$, a first hydrocarbon feed having $C_4$ hydrocarbons and other paraffinic streams to the first zone, feeding at a weight hourly space velocity of 5 h$^{-1}$ to 100 h$^{-1}$, a second hydrocarbon feed having olefinic naphtha stream to the second zone and optionally feeding at a weight hourly space velocity of 40 h$^{-1}$ to 200 h$^{-1}$, a third hydrocarbon feed comprising heavy hydrocarbons to the third zone;

iii. cracking the first, second and third hydrocarbon feeds sequentially, with the help of heat generated by at least one of two heat generating reactions selected from the group consisting of (a) introducing an oxygenate feed to the third zone and converting the oxygenate feed to a gaseous state and (b) burning coke formed in the spent FCC catalyst in a regenerator at a temperature of 650 to 750° C. in the presence of oxygen to generate hot gases and feeding the hot gases from the regenerator to the riser, thereby obtaining light olefins with comparatively higher yield.

Typically, the afore-stated process comprises inclusion of at least one of said third hydrocarbon feed and said oxygenate feed.

Typically, the first feed comprises at least one hydrocarbon feed selected from the group consisting of $C_4$ hydrocarbons and $C_4$-$C_6$ paraffin, the second feed comprises olefinic naphtha having 5 to 12 carbons and the third feed comprises heavy hydrocarbon that includes at least one selected from the group consisting of gas oil, vacuum oil, atmospheric oil/vacuum residue, slurry oil, crack-able cycle oil, and heavy crude.

Typically, the oxygenate feed comprises at least one compound selected from the group consisting of methanol, ethanol and ether.

Particularly, the weight proportion of said $C_4$ hydrocarbon stream varies from 10 to 30 wt %, with respect to the total feed weight, the olefin content in the $C_4$ hydrocarbon stream varies from 30 to 80 vol %, the weight proportion of the paraffinic $C_4$ to $C_6$ stream varies from 5 to 30 wt %, with respect to the total feed weight, the weight proportion of the second feed comprising olefinic naphtha having 5 to 12 carbons varies from 20 to 95 wt %, with respect to the total feed weight, the weight proportion of the third feed varies from 0 to 25 wt %, with respect to the total feed weight and the amount of oxygenate feed varies in the range of 0 to 66 wt %, with respect to the total feed weight. Typically, when the weight proportion of the third feed is 0, the weight proportion of the oxygenate feed is not 0 and when the weight proportion of the oxygen feed is 0, the weight proportion of the third feed is not 0.

Typically, the third feed and the oxygenate feed are fed to the third zone through two separate injection points. The residence time of oxygenate feed is preferably 0.5 sec, based on the oxygenate flow rate.

In accordance with one embodiment of the disclosure, at least one of the first, second and third zones is further divided into at least one subzone depending on the crackability of hydrocarbon feeds.

Particularly, the cracking process comprises the steps of separating the spent FCC catalyst from the cracked gaseous stream, burning the spent FCC catalyst in the regenerator and circulating the hot regenerated catalyst and producing heat nearly equivalent to the heat and pressure required for the endothermal cracking of the hydrocarbon feeds in the riser.

In accordance with another embodiment of the disclosure, the cracking process further comprises the step of re-cycling the regenerated catalyst to the cracker reactor.

Particularly, the disclosure includes providing a FCC catalyst comprising a large pore size zeolite selected from the group consisting of USY, REUSY, Beta and combinations thereof. Typically, the FCC catalyst comprises at least one large pore size zeolite in combination with additives that include medium pore size zeolite selected from the group consisting of ZSM-5, ZSM-11, ZSM-22, SAPO-11 and combinations thereof and the weight proportion of the ZSM-5 zeolite in the additive ranges from 5 to 60 wt % and the weight proportion of the large pore size zeolite varies from 0 to 35 wt %. Particularly, the ZSM-5 zeolite is a phosphate stabilized zeolite having silica to alumina ratio in the range of 20 to 80; more preferably in the range of 30 to 40. Alternatively, the FCC catalyst comprises at least one large pore size zeolite wherein the large pore size zeolite is doped with alkaline earth metal selected from the group consisting of Ca, Mg, Sr and combination thereof and the weight proportion of alkaline earth metal varies from 500 to 20,000 ppm, preferable from 5000 to 10,000 ppm.

The light olefins comprising propylene and ethylene are obtained in accordance with this disclosure in an amount higher than 20 wt % and 6 wt %, respectively.

In accordance with another aspect of this disclosure the process includes the step of preheating the hydrocarbon feeds before introducing them into the riser.

In accordance with yet another embodiment of the disclosure, the process is controlled by at least one of a group of steps comprising preheating the hydrocarbon feeds, controlling the feed rates of the feeds and diluting the feeds with steam.

BRIEF DESCRIPTION OF THE ACCOMPANYING DRAWING

FIG. 1 illustrates a schematic presentation of Thermo Neutral Catalytic Conversion process, in accordance with the present disclosure.

DETAILED DESCRIPTION

The disclosure will now be described with reference to the embodiments shown in the non-limiting accompanying drawings. The embodiments do not limit the scope and ambit of the disclosure. The description relates purely to the exemplary preferred embodiments of the disclosure and its suggested applications.

The diagrams and the description hereto are merely illustrative and only exemplify the disclosure and in no way limit the scope thereof.

Accordingly, a process for improved production of light olefins by catalytically cracking a hydrocarbon feed stock in a single riser is disclosed in the present disclosure wherein the improved production of light olefins from hydrocarbon feedstock is produced under thermally sustained cracking conditions using a single riser system.

As used herein the term "thermo-neutral" refers to a heat-balanced cracking reaction wherein the heat requirement for endothermal cracking is met by heat released by an exothermal cracking of oxygenate or burning the coke deposited on catalyst surface during regeneration process of catalyst.

As used herein the term "fresh feed" refers to a hydrocarbon feed introduced in the reaction zone for conversion and does not include any re-cycled product from that of reaction zone.

As used herein the term "riser" refers to a part of the reactor used in a fluid catalytic process.

As used herein the term, "difficult to crack" refers to crack-ability of olefinic C4 hydrocarbon streams and paraffinic $C_4$-$C_6$ hydrocarbon streams.

As used herein the term "moderate to crack" refers to crack-ability of olefinic naphtha streams ($C_5$-$C_{12}$).

The term "easy to crack" as used in the present disclosure refers to crack-ability of gas oil, vacuum gas oil, atmospheric/vacuum residue, slurry oil, crack-able cycle oil, heavy crude and oxygenate like methanol, ethanol, ether and the like.

The process as disclosed in the present disclosure is a thermo-neutral cracking process wherein the heat requirement for endothermal cracking of hydrocarbon feedstock is accomplished by simultaneously executing the endothermic and exothermic cracking in the same riser. Alternatively, the heat-balanced conditions are provided by burning the coke deposited on cracking catalyst surface in a catalyst regenerator to produce heat equivalent to the heat required for endothermal cracking. The thermo-neutral catalytic conversion of hydrocarbon feedstock in accordance with the present disclosure is typically accomplished in a single riser wherein the cracking conditions including the type and ratio of hydrocarbon feeds, cracking catalyst, temperature, pressure and the riser configuration are optimized to procure light olefins in improved yield.

The above described objects of obtaining light olefins in improved yield by employing thermally sustained cracking reaction in a single riser are accomplished by cracking the hydrocarbon feedstock in a sequential manner wherein diverse range of hydrocarbon feeds having different cracking behavior are catalytically cracked in a sequential manner. The sequential cracking of hydrocarbon feeds is carried out in a way so as to maintain the thermo-neutral or heat-balanced conditions during entire catalytic cracking process.

As described above, the thermo-neutral condition during catalytic cracking is typically sustained by performing the endothermal and exothermal cracking in the same riser or by burning the coke deposited on catalyst surface in the catalyst regenerator. The heat produced during catalyst regeneration or coke burning is further utilized in endothermal cracking of feed.

Typically, the feed stocks having difficult, moderate or easy cracking behavior are employed in the process of the present disclosure. The feeds having difficult to moderate cracking behavior are low coke making feedstock, whereas the feeds having easy crack-ability are usually high coke making feeds or oxygenates that crack exothermally.

Typically, the feeds having difficult crack-ability comprises at least one hydrocarbon feed selected from the group consisting of olefinic $C_4$ hydrocarbons and paraffin having 4 to 6 carbons.

Typically, the feeds having moderate crack-ability comprise olefinic naphtha streams having 5 to 12 carbons.

Typically, the higher coke making feeds having easy crack-ability are heavy hydrocarbons that include at least one selected from the group consisting of gas oil, vacuum gas oil, atmospheric/vacuum residue, slurry oil, crack-able cycle oil and heavy crude.

The hydrocarbon feeds of the present disclosure further comprises oxygenate for exothermal cracking. The oxygenate typically includes at least one selected from the group consisting of methanol, ethanol and ether.

The sequential cracking of hydrocarbon feedstock in accordance with the present disclosure is carried in a single riser. The single riser is a multizone riser having different zones for sequential cracking the hydrocarbon feeds. The multizone riser comprises high, intermediate and low severity zones for sequentially cracking the feeds having difficult, moderate and easy cracking behavior.

The sequential catalytic cracking process of the present disclosure is further described in light of the schematic depiction of thermo-neutral catalytic process (refer to FIG. 1 of the accompanying drawing). The system as employed in the sequential catalytic cracking process of the present disclosure comprises a reaction section 100 and 101, a regeneration section 105 and 106 and a product separation section 110.

The reaction section includes a riser 101 and a reactor 100 wherein feeds having different cracking behavior are introduced separately in a sequential manner particularly from low coke making feed to high coke making or from feeds having difficult crack-ability to feeds having easy crack-ability in the different reaction zones of the single riser.

The thermo-neutral cracking process of the present disclosure comprises at least one reaction selected from the group consisting of (i) endothermally cracking the feeds having $C_4$ hydrocarbons to heavy hydrocarbons, sequentially followed by cracking the exothermal oxygenate or (ii) burning the coke deposited on catalyst surface in a catalyst regenerator to provide heat required for endothermal cracking of feeds having $C_4$ hydrocarbons to heavy hydrocarbons.

The sequential cracking comprises the cracking of $C_4$ hydrocarbons stream 102 at the bottom riser, cracking of paraffinic streams 117 having 4 to 6 carbons at higher elevation of $C_4$ stream injection 102, cracking of predominantly olefin streams like olefinic naphtha streams 121 having 5 to 12 carbons at higher elevation of paraffinic $C_4$-$C_6$ streams injection and optionally, the cracking of methanol 122 or higher coke making heavy feedstock 123 at the top of the riser. The process of the present disclosure comprises inclusion of at least one of the following feeds; oxygenate stream (methanol, ethanol and ether) and third hydrocarbon stream (higher coke making heavy feedstock).

The $C_4$ hydrocarbon feed as injected in the bottom riser is typically a fresh hydrocarbon feed. In one of the embodiments, a recycled $C_4$ hydrocarbon stream 115 generated during sequential catalytic process of the present disclosure is injected with fresh $C_4$ hydrocarbon stream at the bottom riser to maximize light olefin production. The recycled $C_4$ hydrocarbon stream 115 is mixed with fresh $C_4$ hydrocarbon feed 102 only when the recycle $C_4$ hydrocarbon stream 115 comprises minimum of 30 vol % olefin. In another embodiment, the fresh $C_4$ hydrocarbon stream 102 or combination of fresh $C_4$ hydrocarbon stream 102 with recycled stream 115 is diluted with steam prior their injection at the bottom riser.

The $C_4$ stream 102 including the $C_4$ recycle stream 115 is cracked in riser bottom. The cracking of $C_4$ hydrocarbon feed is typically carried out by contacting the feed with a FCC catalyst at suitable cracking conditions of temperature and pressure. The cracking of $C_4$ hydrocarbon feed at the bottom riser is typically carried out at a temperature varying from 650° C. to 750° C.; most preferably at 660° C. to 680° C. The weight hourly space velocity (WHSV) is typically maintained in the range of from 0.2 $hr^{-1}$ to 50 $hr^{-1}$, preferably 1 to 25 $hr^{-1}$ and most preferably 1 to 10 $hr^{-1}$.

The paraffinic stream having 4 to 6 carbons 117 is introduced above $C_4$ injection at the bottom riser having high severity cracking conditions. The paraffinic $C_4$-$C_6$ stream 117 is typically introduced at a distance equivalent to 1 to 1.5 s vapor residence time of $C_4$ stream 102. The weight proportion of paraffinic $C_4$-$C_6$ streams 117 introduced in the riser varies from 5 to 30 wt %, with respect to the weight of total fresh feed wherein initial boiling point (IBP) varies from 35° C. to 50° C. and final boiling point varies from 200° C. to 221° C. The paraffinic stream having aromatic contents not more than 20 vol %, preferably less then 10 vol % is preferred.

The paraffinic stream having 4 to 6 carbons 117 is injected as a fresh feed. In another embodiment, the paraffinic stream having 4 to 6 carbons 117 is injected with a recycle naphtha stream 118 obtained from separation tank 110 of the present disclosure.

The cracking of paraffinic $C_4$-$C_6$ stream 117 is carried out by contacting the feed with the FCC catalyst at a temperature of 630° C. to 690° C., most preferably 650° C. to 680° C. The WHSV during paraffinic cracking is typically maintained in the range of from 5 to 100 $hr^{-1}$, most preferably 50 to 80 $hr^{-1}$.

After introducing paraffinic $C_4$-$C_6$ stream, olefinic naphtha stream having 5 to 12 carbons injected at a point above the paraffinic $C_4$-$C_6$ feedstock injection points so that paraffinic feed ($C_4$-$C_6$) 117 acquires vapor residence time of 1 to 1.5 s. The weight proportion of olefinic naphtha streams ($C_5$-$C_{12}$) 121 introduced in the riser varies from 20 to 95 wt % of total fresh feed, most preferably 50 to 95 wt. %.

The olefin content of $C_5$ to $C_{12}$ olefinic naphtha stream varies from 30 to 70 vol %, most preferable from 45 to 55 vol %. The cracking of moderate to easy cracking feed i.e. olefinic naphtha stream having 5 to 12 carbons 121 is carried out at a temperature of 580° C. to 650° C. The weight hourly space velocity during catalytic cracking of olefinic naphtha feed varies from 5 to 100 hr-1.

The high coke making feed i.e. heavy hydrocarbons are injected at the top of the riser having low severity cracking conditions above olefinic naphtha streams having 5 to 12 carbons 121 injection points. The cracking of high coke making feed is typically carried out at temperature varying in the range of 500° C. to 620° C., most preferably 570° C. to 620° C. and with WHSV varying from 40 to 200 hr-1. The weight proportion of higher coke making heavy hydrocarbon stream 123 injected at the top of the riser varies from 0 to 25 wt %, most preferably 10 to 15 wt %, with respect to the weight of total fresh feed. The high coke making feed is introduced as a fresh feed. In another embodiment, a recycle CSO stream 119 obtained from separation tank 110 is injected with the high coke making feed.

In one of the embodiments, the thermo-neutral sequential cracking of the present disclosure comprises the exothermic cracking of oxygenate feed to provide heat required for the endothermic cracking of hydrocarbon feeds having $C_4$ to heavy hydrocarbons. The oxygenate feed as employed in the present disclosure typically include at least one selected from the group consisting of methanol, ethanol and ether.

Preferably, the methanol 122 in an amount of from 20 to 40 wt %, with respect to the weight of total fresh feed is introduced at the top portion of the riser having low severity cracking conditions. The methanol 122 is injected with high coke making heavy hydrocarbon feed 123 at same elevation of riser, which is typically higher than that of olefinic naphtha stream. The low severity zone of the single riser comprises two separate injection points for injecting heavy hydrocarbon feed and oxygenate separately at the same elevation point. The weight proportion of the third feed varies from 0 to 25 wt %, with respect to the total feed weight and the amount of oxygenate feed varies in the range of 0 to 66 wt %, with respect to the total feed weight. Typically, when the weight proportion of the third feed is 0, the weight proportion of the oxygenate feed is not 0 and when the weight proportion of the oxygen feed is 0, the weight proportion of the third feed is not 0. The residence time of oxygenate feed is typically maintained at 0.5 sec based on only oxygenate flow rate.

The weight ratio of heavy hydrocarbon feed to methanol typically varies from 0 to 1. The cracking of oxygenate feed is typically carried out the top of the riser under low severity cracking conditions that include the cracking temperature of 500° C. to 620° C., most preferably 500° C. to 600° C. and weight hourly space velocity of 40 $hr^{-1}$ to 200 $hr^{-1}$. The pressure in the top of riser reactor is in the range of 0.5 to 3.0 bar (g).

The each severity zone of the single riser of the present disclosure is further subdivided into more than one subzone depending on the crack-ability of individual feedstock. The operation control of each zone is provided and maintained by altering the feed preheat temperature and steam dilution to the combined hydrocarbon stream entering to each zone. The desired WHSV in each zone is additionally achieved by altering the riser diameter, length and injection of the hydrocarbon and dilution steam.

The product vapors coming out of the reactor section 100, wherein the spent catalyst is separated from cracking products, goes to the separation section 110 through conduit 109. The separation section 110 consists of fractionation columns and gas concentration section. The cracking products are further separated into different products like dry gas 111, ethylene 112, propylene 113, $C_4$ 116, naphtha 120, light cycle oil (LCO) 114 and clarified slurry oil (CSO) 124. Out of these streams, a portion or complete $C_4$ stream 115 is recycled back through conduit and injected at the bottom riser along with fresh $C_4$ stream 102 to increase the yield of $C_2$ and $C_3$ olefin products. A portion or complete naphtha stream 118 is also recycled back through conduit along with fresh Paraffinic $C_4$-$C_6$ stream 117 to provide an additional conversion across the overall process system. A portion or complete CSO stream 119 is recycled back through conduit along with fresh heavy hydrocarbon feed 123 to provide additional coke deposition on catalyst to satisfy heat requirement.

The spent catalyst recovered from reactor 100 passes from reactor stripper section through spent catalyst stand pipe 104 and is introduced to the regeneration section which consists of a combustor 106 and regenerator vessels 105. In the regenerator section, the catalyst is contacted with oxygen containing gas such as air 107, at the temperature range of 650 to 750° C., pressure of 1 to 3 bar(g) to remove coke deposited on the spent catalyst. The oxygen containing gas is introduced into the regenerator through conduit 107 and combustion gases pass from regenerator by way of conduit 108. The regenerated hot catalyst then passes from regenerator to the riser through regenerated catalyst standpipe 103. The heat generated during regeneration of spent catalyst is further utilized for heating the feeds while contacting feeds with regenerated catalyst. The sequential thermo-neutral catalytic process of the present disclosure produces light olefins that typically include ethylene and propylene in an amount higher than 6 wt % and 20 wt % respectively.

The catalyst as employed in the present disclosure for cracking the hydrocarbon feeds under thermo-neutral conditions is typically a FCC catalyst comprising at least one large pore zeolite selected from the group consisting of USY REUSY, beta or combination thereof. The FCC catalyst as employed in the present disclosure is further used in combination with an additive (pentasil zeolite) selected from the group consisting of ZSM-5, ZSM-11, ZSM-22, SAPO-11 and combinations thereof. Typically, the additive is a medium pore zeolite. The ZSM 5-additive is typically a phosphate stabilized zeolite having silica to alumina ratio in the range of 20 to 80, most preferably 30 to 40. Typically, the weight proportion of the ZSM-5 zeolite in the additive varies from 5 to 60 wt %, most preferably 20 to 30 wt %; whereas the weight percent of the large pore size zeolite ranges from 0 to 35 wt %. The product selectivity of FCC catalyst is further enhanced by doping the additive with alkaline earth metals that typically include at least one selected from the group consisting of Ca, Mg and Sr. The concentration of alkaline earth metal typically varies from 500 to 20000 ppm, more preferably from 5000 to 10000 ppm, without adversely affecting activity of catalyst.

The FCC catalyst as employed in the cracking process of the present disclosure is prepared by employing the process as disclosed in our co-pending Indian patent application no. 1955/MUM/2011 and PCT application PCT/IN2011/000599. However, ZSM-5 zeolite and ReUSY or USY based catalyst available in commercial markets can also be used in the present disclosure.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Illustrative Example

According to the present disclosure, there is provided a sequential multizone, multifeed & thermo neutral catalytic cracking process. The process comprising of sequential multizone reaction section in a single riser divided into high, intermediate and low severity zones for sequential cracking of wide range of feedstock from $C_4$ to residue including both olefinic and paraffinic naphtha streams as further distinguished by difficult to crack, moderate to crack, easy to crack and high coke making feedstock. (refer to FIG. 1 for Schematic depiction of Thermo Neutral Catalytic Conversion (TNC2) process). The operational control of each zone is maintained by altering the feed preheat temperature, feedstock flow rate and steam dilution to the combined hydrocarbon stream entering each zone and whereas the desired WHSV in each zone is additionally achieved in the design by altering the riser diameter, length and location of the injection point for hydrocarbon and dilution steam.

The properties of different feedstock used for different examples are given in Table 1.

TABLE 1

Characterization of different feedstock

| Feed Density @ 15 C. | Kg/m3 | Light Coker Naphtha (LCN) 682.2 | Clarified Slurry Oil (CSO) 1071 |
|---|---|---|---|
| Distillation | | Volume % | Weight % |
| Initial Boiling Point | C. | 39 | 188 |
| 5% | C. | — | 294 |
| −30% | C. | 56 | 360.5 |
| 50% | C. | 65 | 390 |
| 70% | C. | 76 | 424 |
| 90% | C. | 87 | 487 |
| FBP | C. | 101 | 605 |

Example 1

This example illustrates the concept of thermal neutrality with the regeneration of catalyst by combining endothermic cracking of Light Coker Naphtha (LCN) with exothermic cracking of Methanol over hydrothermally deactivated ZSM-5 additive. The physico-chemical properties of fresh ZSM-5 additive are given in Table 2.

TABLE 2

Physico-chemical properties of ZSM-5 zeolite based catalyst

| | ZSM-5 based catalyst |
|---|---|
| Total Surface area, m2/gm | 140 |
| Total zeolite Surface area, $m^2/g$ | 110 |
| Chemical Analysis, wt. % | |
| $Al_2O_3$ | 18.70 |
| $Na_2O$ | 0.11 |
| $P_2O_5$ | 11.98 |
| ABD, g/cc | 0.75 |
| Attrition Index(ASTM) | 3.12 |
| Particle Size Distribution, wt. % | |
| −40 micron | 6 |
| −60 | 28 |
| −80 | 53 |
| −100 | 72 |
| APS | 77 |

The above ZSM-5 additive was hydro thermally deactivated separately at 800° C., atmospheric pressure for 20 hours using 100% steam. 10 g of hydrothermally deactivated ZSM-5 additive was loaded in fixed fluid bed micro reactor. The micro reactor is electrically heated to maintain the catalyst bed temperature of 620° C. The LCN as mentioned in Table 1 was cracked in the fluidized bed reactor for time of stream (TOS) of 30 seconds at 620° C. temperature and atmospheric pressure wherein vapor residence time is lower than 0.5 sec. Immediately after cracking, catalyst bed was stripped with nitrogen for removing all strippable hydrocarbons and cracked gas along with strippable hydrocarbon which was collected and measured under chilling condition was analyzed to get gas yield. The coke on catalyst was burnt off using air at 750° C. temperature, wherein coke was measured by passing flue gas to on-line IR analyzer. The collected liquid product was analyzed in typical SIMDIST analyzer to get different liquid product. This experiment gave yield pattern of LCN as mentioned in column-1 of Table 3.

As explained above, another experiment was carried out without burning of coke deposited on catalyst. Once stripping was over, methanol was cracked on spent catalyst bed for TOS of 30 sec at 620° C. temperature and atmospheric pressure wherein vapor residence time was less than 0.5 sec. The yield pattern from Methanol cracking is summarized in column-2 of Table 3.

TABLE 3

Yields from heat neutral cracking of LCN and Methanol

| Yield, wt. % | LCN Column-1 | Methanol Column-2 | LCN & Methanol (1:1.40) Column-3 |
|---|---|---|---|
| Dry gas (excluding ethylene) | 4.82 | 5.57 | 5.26 |
| Ethylene | 10.58 | 10.48 | 10.52 |
| Propylene | 19.73 | 14.11 | 16.45 |
| | 38.14 | 23.67 | 29.70 |
| Gasoline (C5-221° C.) | 43.63 | 4.58 | 20.85 |
| Coke | 2.09 | 0.7 | 1.28 |
| 221° C.+ (water) | 0.74 | (55) | 32.39 |

The above data shows that even though spent additive have some coke due to cracking of LCN, the residual activity of additive is enough for selectively cracking of methanol. Therefore, sequential cracking of LCN followed by methanol provide better yield of olefin from methanol even at very high temperature. The coke make (~2.09 wt. %) from Light Coke Naphtha feed is low as compared to the required coke of 5.7 wt. % (on feed) to supply the total heat required for preheating, vaporization and cracking the feed. The net heat demand for Light Coker naphtha is 346 Kcal/kg. The combined heat released from cracking of methanol alone and from burning its coke (0.7 wt. % on feed) is more than required for preheating and vaporizing methanol; net surplus heat is 192.2 Kcal per kg of methanol. The surplus heat released by cracking 1.4 kg of methanol is sufficient to preheat, vaporize and crack one kg of Light Coker naphtha. Hence, 1 kg of LCN is required to be cracked with 1.40 kg of methanol to make process heat neutral and estimated products are summarized in column-3 of Table 3. Therefore, LCN is to be cracked followed by cracking of methanol with residence time of less than one second. Heat generated in the regenerator from burning of the coke deposited during sequential cracking of LCN and Methanol on the catalyst also contributes in meeting the heat demand of the process.

TABLE 4

Heat neutrality of Cracking LCN with Methanol

|  |  | LCN | Methanol | LCN& Methanol (1:1.40) |
|---|---|---|---|---|
| Reactor temperature | ° C. | 620 | 620 | 620 |
| Regent temperature | ° C. | 700 | 700 | 700 |
| Cat to oil | Wt/wt. | 13.33 | 12.28 | 13.42 |
| Actual Coke yield | Wt % feed | 2.09 | 0.7 | 0.81 |
| Heat required for heating and vaporizing feed | Kcal | 328.23 | 364.46 | 799.43 |
| Heat of cracking | Kcal | 91.35 | −560 | −632.66 |
| Heat from coke burning | Kcal | 153.74 | 72.09 | 166.76 |
| Net Heat Demand | Kcal | 265.8 | −266.0 | 0.0 |
| Required Coke for heat balance | Wt % feed | 5.70 | −1.90 | 1.27 |

Example 2

This example further illustrates thermal neutrality by combining endothermic cracking of LCN with cracking of heavy feed like clarified Slurry oil (CSO) over mixed catalyst consisting of equal proportions of hydrothermally deactivated ZSM-5 additive and ultra-stable Y zeolite based FCC catalyst. CSO is a product from FCC unit from cracking of vacuum gas oil. In this experiment, ZSM-5 additive as mentioned in Table 2 has been used. However, physico-chemical properties of FCC catalyst used in this experiment are shown in Table 5.

TABLE 5

Physico-chemical properties of fresh FCC catalyst

|  | FCC catalyst |
|---|---|
| Total Surface area, m²/g | 336 |
| Total zeolite Surface area, m²/g | 226 |
| Pore volume, cc/g | 0.35 |
| ABD, g/cc | 0.78 |
| Chemical Analysis, wt. % |  |
| $Al_2O_3$ | 29.37 |
| $Na_2O$ | 0.28 |
| $Re_2O_3$ | 0.85 |

TABLE 5-continued

Physico-chemical properties of fresh FCC catalyst

|  | FCC catalyst |
|---|---|
| Particle Size Distribution, wt. % |  |
| −40 micron | 4 |
| −80 | 67 |
| APS | 70 |
| Attrition Index(ASTM) | 2.52 |

LCN and clarified slurry oil (CSO) were cracked separately in fixed fluid bed reactor in presence of equal amount of ZSM-5 additive and FCC catalyst and yield pattern were summarized in Table 6.

TABLE 6

Yield from cracking light Coker naphtha with heavy feed

| Yields, wt. % | LCN Column-1 | CSO Column-2 | LCN& CSO (1:0.495) Column-3 |
|---|---|---|---|
| Dry gas (excluding ethylene) | 4.15 | 4.50 | 4.27 |
| Ethylene | 9.24 | 2.23 | 6.92 |
| Propylene | 20.02 | 3.03 | 14.39 |
| LPG | 37.77 | 5.56 | 27.11 |
| Gasoline (C5-221° C.) | 43.63 | 4.05 | 30.52 |
| Coke | 2.41 | 10.72 | 5.16 |
| 221° C.+ | 2.8 | 72.94 | 26.02 |

The coke make (~2.41 wt. %) from Light Coke Naphtha feed is low as compared to the required coke of 5.7 wt. % (on feed) to supply the total heat required for preheating, vaporization and cracking the feed. As shown in Table 7, the net heat demand for Light Coker naphtha is 242 Kcal/kg. The additional coke required for heat balancing is provided by cracking of heavy cycle oil which makes 10.72 wt. %. The heat released by burning the coke from heavy feed is more than required for preheating and vaporizing heavy feed; net surplus heat is 490 Kcal per kg of the heavy feed. The surplus heat released by cracking 0.495 kg of heavy feed is sufficient to preheat, vaporize and crack one kg of Light Coker naphtha. Thus cracking of LCN in combination with a heavy feed like Cycle oil makes the process heat neutral i.e. it does not require burning fuel oil/torch oil in the regenerator to supply external heat to run the process

TABLE 7

Heat neutral cracking with regeneration by combining Light Coker feed with Heavy feed

|  |  | LCN Column-1 | CSO Column-2 | LCN& CSO (1:0.495) Column-3 |
|---|---|---|---|---|
| Reactor temperature | ° C. | 620 | 620 | 620 |
| Regenerator temperature | ° C. | 700 | 700 | 700 |
| Cat to oil | Wt/wt. | 15.48 | 13.83 | 14.80 |
| Kinetic Coke yield | Wt % feed | 2.41 | 10.726 | 5.02 |
| Heat required for heating/vaporizing feed | Kcal | 328.23 | 145.18 | 473.41 |
| Heat of cracking | Kcal | 91.35 | 2.83 | 94.18 |
| Heat from burning available coke | Kcal | 177.28 | 390.57 | 567.85 |
| Net Heat Demand after coke burning | Kcal | 242.30 | −242.30 | 0.0 |

TABLE 7-continued

Heat neutral cracking with regeneration by combining Light Coker feed with Heavy feed

|  |  | LCN Column-1 | CSO Column-2 | LCN& CSO (1:0.495) Column-3 |
|---|---|---|---|---|
| Coke for Heat balance | Wt % feed | 5.70 | 4.07 | 5.16 |

Example 3

This example illustrate concept of sequential cracking of feedstock depending on their crack-ability. LCN and n-hexane feedstock were separately cracked in fixed fluid bed micro reactor at different reactor temperature in presence of ZSM-5 zeolite based catalyst as explained in example 1. The yield patterns are summarized in Table 8. As shown in the Table 8, when both light Coker naphtha (LCN) and N-hexane are cracked at same conditions of 620° C., LCN cracks to produce high yield of propylene and ethylene with lower coke and dry gas yield, whereas N-hexane has lower yields of propylene and ethylene under same conditions. Increasing cracking severity (reaction temperature of 675° C.) improves the yield of Propylene and Ethylene for low cracking N-hexane whereas easily crack-able LCN substantially increases the yield of the undesirable products like dry gas and coke as compared to improvement in the yields of light olefins. Thus, feeds having different crack-ability need to be injected at different locations to provide optimum cracking severity to obtain maximum yields of Light olefins and to minimize undesirable products like coke and dry gas. In a single riser, this can be achieved by sequential cracking of N-hexane followed by LCN at two different locations along the riser length. As described in process description section, riser bottom temperature is in the range of 650 to 750 degree C. and catalyst has highest activity, hence, riser bottom is the ideal location to inject least crack-able material like $C_4$ streams, saturated $C_4$-$C_6$ hydrocarbons etc. In summary, the high active catalyst and high severity zones at riser bottom provide flexibility to crack least crack-able hydrocarbon materials in a compact configuration using single riser and reactor.

TABLE 8

Importance of sequential cracking in single riser - effect of operating severity

| Catalyst | ZSM 5 | ZSM 5 | ZSM 5 | ZSM 5 |
|---|---|---|---|---|
| Feed | LCN | LCN | N-HEXANE | N-HEXANE |
| Reactor Temperature, ° C. | 620 | 675 | 620 | 675 |
| Catalyst-to-Oil, wt./wt. | 13.33 | 13.33 | 13.33 | 13.33 |
| YIELDS, wt. %: |  |  |  |  |
| Coke | 2.09 | 6.67 | 1.88 | 3.93 |
| Dry gas(excluding ethylene) | 4.82 | 8.71 | 7.17 | 13.04 |
| Ethylene | 10.58 | 14.20 | 7.40 | 11.56 |
| Propylene | 19.73 | 23.32 | 13.06 | 17.84 |
| LPG | 38.14 | 39.47 | 26.25 | 31.39 |
| Gasoline (35-221° C.) | 43.63 | 30.44 | 57.12 | 39.96 |

Example 4

This example illustrates importance of sequential injection over co-injection of feedstock. To make the process heat balanced, very high coke yielding (heavy) feeds are required to be cracked along with lighter feeds since lighter feeds do not make sufficient coke. In the single riser, if heavy feeds are injected prior to the lighter feeds or are co-injected at same location, the heavy feed will coke and deactivate the catalyst and will render it ineffective for cracking lighter feeds, ultimately deteriorating the overall yields. Using experimental setup as explained in example 1, cracking data for LCN and CSO were generated at 600 degree reaction temperature and atmospheric pressure, catalyst to oil ratio of 13.33 using TOS of 30 sec. Results are summarized in Table 9. Furthermore, LCN and CSO were mixed in equal proportion and co-injected into reactor maintaining reaction conditions as above. In case, LCN is cracked followed by CSO at above condition, the expected yield is estimated to be average of two individual yields as shown in column-3 of Table 9. As can be seen from Table 9, in case co-feeding, propylene yield was lower than the yields obtained by sequential feeding. Moreover, overall conversion also comes down while co-cracking the two feeds. It is worth to mention that sequential cracking in reverse order i.e., COS cracking followed by LCN cracking will deteriorate the yield pattern in comparison with co-feeding. This is ensured that the high coke making (heavy) feedstock needs to be introduced in the last zone of the riser.

TABLE 9

Effect of co-injecting heavier and lighter feeds on yields.

| Catalyst Name | ZSM 5 | ZSM 5 | ZSM 5 | ZSM 5 |
|---|---|---|---|---|
| Feed Name | CSO | LCN | Averaged for LCN and CSO | 50:50 CSO:LCN |
| Reactor Temperature, ° C. | 600 | 600 |  | 600 |
| Catalyst-to-Oil, wt./wt. | 13.33 | 13.33 | 13.33 | 13.33 |
|  | Column-1 | Column-2 | Column-3 | Column-4 |
| Yields, wt. %: |  |  |  |  |
| Coke | 15.11 | 1.78 | 8.44 | 7.49 |
| Dry gas(excluding ethylene) | 1.90 | 2.52 | 2.21 | 3.05 |
| Ethylene | 1.39 | 8.59 | 4.99 | 5.06 |
| Propane | 0.22 | 3.20 | 1.71 | 2.45 |
| Propylene | 1.72 | 20.94 | 11.33 | 8.80 |
| LPG | 2.92 | 40.00 | 21.45 | 17.04 |
| Gasoline | 2.21 | 46.10 | 24.15 | 16.38 |
| 221° C.+ | 76.48 | 1.05 | 38.77 | 51.02 |

Example 5

This example illustrate that the optimum catalyst mix is required to maximize yield of light olefins in a single riser from feeds having wide difference in crack ability. As per prior art, ZSM 5 zeolite based catalyst gives highest propylene yield and conversion for light feeds like LCN and N-hexane while heavy feed like clarified slurry oil (CSO) gives highest conversion with Y zeolite based catalyst. To find an optimum mix of ZSM-5 and Y zeolite, each of the three feeds viz. LCN, N-Hexane and CSO were cracked with each of 50 wt. % ZSM 5 crystal, 45 wt. % Y Zeolite crystal and 25 wt. % ZSM 5 crystal with 22.5 wt. % Y Zeolite crystal mixture based catalyst. The typical properties of ZSM-5 and USY based catalyst are shown in previous examples. Different experimental data generated in experimental set up which is explained in example-1. From table 10, it is observed that for light feeds like LCN and N-hexane, yield of light olefins and conversion are similar with 50 wt. % ZSM 5 crystal and with 25 wt. % ZSM 5 crystal+22.5 wt. % Y Zeolite crystal, but with 45 wt. % Y Zeolite crystal, the light olefin yields and conversion are the lowest from the three catalyst mixes. For heavy feed CSO, though 45 wt. % Y Zeolite crystal gives highest conversion but the yield of light olefins are lower than those obtained with 25 wt. % ZSM 5 crystal+22.5 wt. % Y Zeolite crystal mix. With CSO as feed, 50 wt. % ZSM 5 crystals give lowest conversion and lowest light olefin yields. Overall, it is observed that for light feeds, the yields of light olefins are similar for 45 wt. % Y Zeolite crystal and for 25 wt. % ZSM 5 crystal+22.5 wt. % Y Zeolite crystal mixtures and is better than with 45 wt. % Y Zeolite crystal case. For CSO also, mixture of 25 wt. % ZSM 5 crystal+22.5 wt. % Y Zeolite crystal gives highest yield of light olefins though conversion is lower than with 45 wt. % Y Zeolite crystal. Therefore, catalyst composition needs to be selected depending on the feed composition to be cracked in riser.

TABLE 10

Optimum catalyst composition for different feeds

| Catalyst Feed | 50 wt. % ZSM 5 crystal LCN | 45 wt. % Y Zeolite crystal LCN | 25 wt. % ZSM 5 crystal + 22.5 wt. % Y Zeolite crystal LCN | 50 wt.% ZSM 5 crystal N-HEXANE | 45 wt. % Y Zeolite crystal N-HEXANE | 25 wt. % ZSM 5 crystal + 22.5 wt. % Y Zeolite crystal N-HEXANE | 50 wt. % ZSM 5 crystal CSO | 45 wt. % Y Zeolite crystal CSO | 25 wt.% ZSM 5 crystal + 22.5 wt.% Y Zeolite crystal CSO |
|---|---|---|---|---|---|---|---|---|---|
| Reactor Temperature, ° C. | 620 | 620 | 620 | 675 | 675 | 675.0 | 620.0 | 620 | 620 |
| Catalyst-to-Oil, wt./wt. | 13.33 | 13.33 | 13.33 | 13.33 | 13.33 | 13.33 | 13.33 | 13.33 | 13.33 |
| YIELDS, wt. %: | | | | | | | | | |
| Coke | 2.10 | 2.16 | 2.41 | 3.93 | 3.11 | 4.13 | 11.94 | 12.07 | 10.73 |
| Dry Gas | 4.82 | 3.79 | 4.15 | 13.04 | 9.71 | 12.77 | 2.76 | 5.99 | 4.49 |
| Ethylene | 10.58 | 3.67 | 9.24 | 11.56 | 7.98 | 10.79 | 1.70 | 1.73 | 2.23 |
| Propylene | 19.73 | 13.88 | 20.03 | 17.84 | 13.63 | 18.87 | 2.03 | 2.71 | 3.03 |
| LPG | 38.14 | 28.27 | 37.77 | 31.39 | 23.48 | 32.43 | 3.51 | 5.84 | 5.56 |
| Gasoline | 43.63 | 60.60 | 45.45 | 39.96 | 55.45 | 39.14 | 2.87 | 6.16 | 4.05 |
| 221° C.+ | 0.74 | 1.51 | 0.98 | 0.13 | 0.28 | 0.83 | 77.22 | 68.21 | 72.94 |

Example 6

This example illustrates the performance of ZSM-5 zeolite based catalyst for improving yields of light olefins. Three different ZSM-5 based catalyst i.e, (i) commercial ZSM-5 additive as shown in example 1, an ultra-stable ZSM 5 zeolite based catalyst as disclosed in PCT application PCT/IN2011/000599 and alkaline metal modified ZSM 5 as disclosed in Indian patent application no. 1955/MUM/2011 were evaluated in the experimental set up as explained in example 1. The performance of these catalysts are compared for LCN as feed as shown in Table 11. As compared to the commercially available ZSM 5, ultrastable ZSM 5 based additive is shown to give highest yields of light olefins. Alkaline metal doped commercial ZSM 5 additive produces light olefin yields comparable to commercial ZSM 5 additive but additionally reduces yield of dry gas. Thus the alkaline metal modified commercial ZSM 5 can be used to reduce Dry gas yield while maximizing C3 olefin yield at high severity.

TABLE 11

Effect of ZSM-5 zeolite stabilization process

| Catalyst | Commercial ZSM 5 Additive as example 1 | Ca modified ZSM 5 (10000 ppm Ca content) (Indian patent appl. no. 1955/MUM/2011) | Ultrastable ZSM-5 additive (PCT/IN2011/000599) |
|---|---|---|---|
| ZSM 5 crystal content, wt. % | 50 | 50 | 40 |
| Feed | LCN | LCN | LCN |
| Reactor Temperature, ° C. | 620 | 620 | 620 |
| Catalyst-to-Oil, wt./wt. | 13.33 | 13.33 | 13.33 |
| Yields, wt. %; | | | |
| Coke | 2.09 | 2.00 | 2.12 |
| Dry gas(excluding ethylene) | 4.82 | 3.37 | 5.28 |
| Ethylene | 10.58 | 8.70 | 11.91 |
| Propylene | 19.73 | 20.41 | 20.31 |
| LPG | 38.14 | 36.60 | 40.69 |
| Gasoline | 43.63 | 48.50 | 38.18 |
| 221° C. | 0.74 | 0.83 | 1.82 |

Example 7

This example illustrates the possibility of using different heavier hydrocarbon feedstock in place of CSO as described in previous examples. Crude oil which are difficult to process because of its high metal content, high TAN value, high viscosity or low API value are called opportunity crude. These crudes are available at lower market price than other light crude oil. Internationally known feedstock such as Mangla, DOBA, DAR were cracked in experimental set up described in example 1 using FCC equilibrium(Ecat) catalyst at 600° C., atmospheric pressure, TOS of 30 sec at 13.33 catalyst to oil ratio. The major physic-chemical properties of Ecat and cracking data for various feed are given in Table 12 and 12A respectively.

TABLE 12

Physico-chemical properties of Ecat

| Parameters | |
|---|---|
| Total Surface Area, m$^2$/g | 166 |
| Total Zeolite Surface area, m$^2$/g | 105 |
| MAT activity, wt. % | 72 |
| Metals on Ecat, PPM | |
| Nickel | 339 |
| Vanadium | 670 |
| Phosphorus | 1.36 |
| Al$_2$O$_3$ | 38.2 |
| Re$_2$O$_3$ | 0.79 |
| Particle Size Distribution, micron | |
| −20 | 0 |
| −40 | 2 |
| −45 | 3 |
| −80 | 32 |
| APS | 96 |

As can be seen from Table 12A, processing these crudes in place of CSO in present disclosure will not only provide required coke yield for heat balance but also improve overall yield slate. It is observed that, compared to CSO, coke yield is almost same for these crudes however, LPG, propylene and gasoline yields are much higher. This makes processing of opportunity crude oils in place of CSO much more attractive.

TABLE 12A

Direct crude processing as high coke making feedstock

| Catalyst | E-CAT | E-CAT | E-CAT | E-CAT |
|---|---|---|---|---|
| Feed | Mangla | DOBA | DAR | CSO |
| Reactor Temperature, ° C. | 600 | 600 | 600 | 600 |
| Catalyst-to-Oil, wt./wt. | 13.33 | 13.33 | 13.33 | 13.33 |
| Yields, wt. %: | | | | |
| Coke | 16.76 | 16.83 | 16.82 | 16.97 |
| Dry gas (excluding ethylene) | 3.82 | 4.29 | 4.60 | 4.74 |
| Ethylene | 6.10 | 5.04 | 5.78 | 1.95 |
| Propylene | 19.96 | 15.41 | 18.05 | 2.88 |
| LPG | 44.61 | 35.06 | 39.67 | 6.12 |
| Gasoline | 19.44 | 23.44 | 21.43 | 4.71 |
| Other Products | 9.27 | 15.35 | 11.69 | 65.52 |

Technical Advantages

Technical advantages of the present disclosure lie in providing a process for catalytic conversion of hydrocarbon feedstock to lower olefins with improved yield that involve:

1. catalytic cracking of diverse range of hydrocarbon feedstocks having difficult, moderate and easy cracking behavior in a sequential manner;
2. the sequential cracking of diverse range of hydrocarbon feedstocks in a single riser wherein the single riser being divided into multizones for executing the sequential cracking; and
3. thermo-neutral conditions during entire catalytic cracking process wherein the thermo-neutral conditions are accomplished in the single riser reactor by employing sequential cracking of hydrocarbon feeds or sequentially cracking the feeds in the multizones riser followed by burning the coke deposited on the catalyst surface to provide the heat required for endothermal cracking.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

"Whenever a range of values is specified, a value up to 10% below and above the lowest and highest numerical value respectively, of the specified range, is included in the scope of the disclosure".

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

Any discussion of documents, acts, materials, devices, articles or the like that has been included in this specification is solely for the purpose of providing a context for the invention. It is not to be taken as an admission that any or all of these matters form part of the prior art base or were common general knowledge in the field relevant to the invention as it existed anywhere before the priority date of this application.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The invention claimed is:

1. A process for obtaining light olefins comprising the following steps:
   i. providing a pre-heated cracking reactor comprising a riser maintained at a pressure in the range of 0.5 to 3 bar, charged with a solid acidic FCC catalyst, said riser being provided with at least three temperature zones;
   a first zone operative at the bottom of the riser having a temperature in the range of 650° C. to 750° C.,
   a second intermediate zone having a temperature in the range of 580° C. to 650° C. operative at a point above the first zone and
   a third zone operative at the top of the riser, above the second zone, having a temperature in the range of 500° C. to 620° C.;
   ii. feeding a first hydrocarbon feed comprising C4 hydrocarbons and a paraffinic stream to the first zone at a weight hourly space velocity of 0.2 h$^{-1}$ to 50 h$^{-1}$,
   feeding a second hydrocarbon feed comprising olefinic naphtha to the second intermediate zone at a weight hourly space velocity of 5 h$^{-1}$ to 100 h$^{-1}$, feeding a third hydrocarbon feed comprising heavy hydrocarbons to the third zone at a weight hourly space velocity of 40 h$^{-1}$ to 200 h$^{-1}$;

iii. cracking the first, second and third hydrocarbon feeds sequentially along the riser, thereby producing light olefins;

wherein additional heat is provided to the riser by:
introducing an oxygenate feed comprising methanol to the third zone and converting the oxygenate feed to olefins; and optionally burning coke formed in a spent FCC catalyst in a regenerator at a temperature of 650 to 750° C. in the presence of oxygen to generate hot gases and feeding the hot gases to the first zone.

2. The process as claimed in claim 1, wherein
said paraffinic stream comprises 4 to 6 carbons;
the second hydrocarbon feed comprises C5-C12 olefinic naphtha;
the third hydrocarbon feed comprises at least one heavy hydrocarbon selected from the group consisting of gas oil, vacuum oil, atmospheric oil/vacuum residue, slurry oil, crack-able cycle oil and heavy crude; and
the oxygenate feed further comprises at least one of ethanol and ether.

3. The process as claimed in claim 1, wherein
the weight proportion of said C4 hydrocarbon stream varies from 10 to 30 wt %, with respect to the total feed weight and comprises an olefin content from 30 to 80 vol %;
the weight proportion of the paraffinic stream varies from 5 to 30 wt %, with respect to the total feed weight;
the weight proportion of the second hydrocarbon feed varies from 20 to 95 wt %, with respect to the total feed weight;
the weight proportion of the third hydrocarbon feed varies from up to 25 wt %, with respect to the total feed weight; and
the amount of the oxygenate feed varies in the range of from up to 66 wt %, with respect to the total feed weight.

4. The process as claimed in claim 1, wherein the third hydrocarbon feed and the oxygenate feed are fed to the third zone through two separate injection points.

5. The process as claimed in claim 1, wherein the residence time of the oxygenate feed is 0.5 sec, based on the oxygenate feed flow rate.

6. The process as claimed in claim 1, wherein the oxygenate feed is converted to ethylene and propylene.

7. The process as claimed in claim 1, wherein at least one of the first, second, and third zone is further divided into at least one subzone.

8. The process as claimed in claim 1 wherein the cracking process comprises the stops of separating a spent FCC catalyst from the cracked gaseous stream.

9. The process as claimed in claim 1, wherein the step of burning the spent FCC catalyst in the regenerator includes the step of obtaining hot regenerated catalyst and producing heat nearly equivalent to the heat required for endothermic cracking of the hydrocarbon feeds in the riser and a pressure in the range of 1 to 3 bar.

10. The process as claimed in claim 1, wherein the cracking process further comprises recycling a regenerated catalyst to the cracking reactor.

11. The process as claimed in claim 1, wherein the FCC catalyst comprises a large pore size zeolite selected from the group consisting of USY, REUSY, Beta and combinations thereof, wherein the large pore size zeolite is further doped with alkaline earth metal(s) selected from the group consisting of Ca, Mg, Sr and combinations thereof, such that the weight proportion of the alkaline earth metal(s) vary from 500 to 20,000 ppm.

12. The process as claimed in claim 1, wherein the FCC catalyst comprises at least one large pore size zeolite in combination with additives that include medium pore size zeolite selected from the group consisting of ZSM-5, ZSM-11, ZSM-22, SAPO-11 and combinations thereof, wherein the medium pore size zeolite additive is a phosphate stabilized zeolite comprising a silica to alumina ratio in the range of 20 to 80; and wherein the weight proportion of the medium pore size zeolite in the additive ranges from 5 to 60 wt % and the weight proportion of said large pore size zeolite ranges from 0.1 to 35 wt %.

13. The process as claimed in claim 1, wherein the light olefins comprising propylene and ethylene are obtained in an amount higher than 20 wt % and 6 wt %, respectively.

14. The process as claimed in claim 1, which includes the step of preheating the hydrocarbon feeds before introducing them into the riser.

15. The process as claimed in claim 1, further comprising controlling at least one of a group of steps comprising preheating the hydrocarbon feeds, controlling the feed rates of the feeds and diluting the feeds with steam.

* * * * *